US00PP21258P2

(12) United States Plant Patent
Lemon

(10) Patent No.: US PP21,258 P2
(45) Date of Patent: Aug. 31, 2010

(54) ***GERANIUM* PLANT NAMED 'OGLGER3147'**

(50) Latin Name: *Pelargonium×hortorum*
Varietal Denomination: Oglger3147

(75) Inventor: David G. Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 16 days.

(21) Appl. No.: 12/316,452

(22) Filed: Dec. 12, 2008

(51) Int. Cl.
*A01H 5/00* (2006.01)

(52) U.S. Cl. ..... Plt./328

(58) Field of Classification Search ..... Plt./328
See application file for complete search history.

(56) References Cited

U.S. PATENT DOCUMENTS

PP12,411 P2 * 2/2002 Hanes ..... Plt./329

* cited by examiner

*Primary Examiner*—Wendy C Haas
(74) *Attorney, Agent, or Firm*—C. A. Whealy

(57) ABSTRACT

A new and distinct cultivar of Zonal *Geranium* plant named 'Oglger3147', characterized by its compact, upright, outwardly spreading and mounded plant habit; freely branching habit; freely flowering habit; dark green-colored leaves; bright cherry rose-colored flowers; and good garden performance.

1 Drawing Sheet

Botanical designation: *Pelargonium×hortorum*.
Cultivar denomination: 'Oglger3147'.

BACKGROUND OF THE INVENTION

The present invention relates to a new and distinct cultivar of Zonal *Geranium* plant, botanically known as *Pelargonium×hortorum*, and hereinafter referred to by the name 'Oglger3147'.

The new Zonal *Geranium* plant is a product of a planned breeding program conducted by the Inventor in Lompoc, Calif. The objective of the breeding program is to create new compact Zonal *Geranium* cultivars with attractive and unique flower coloration.

The new Zonal *Geranium* plant originated from a cross-pollination made by the Inventor in March, 2000 in Lompoc, Calif. of a proprietary selection of *Pelargonium×hortorum* identified as code number 9952, not patented, as the female, or seed, parent with a proprietary selection of *Pelargonium×hortorum* identified as code number 9925, not patented, as the male, or pollen, parent. The new Zonal *Geranium* was discovered and selected by the Inventor as a single flowering plant from within the progeny of the stated cross-pollination in a controlled greenhouse environment in Lompoc, California in March, 2001.

Asexual reproduction of the new Zonal *Geranium* plant by vegetative terminal cuttings in a controlled greenhouse environment in Connellsville, Pa. since April, 2002, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglger3147'. These characteristics in combination distinguish 'Oglger3147' as a new and distinct cultivar of Zonal *Geranium:*

1. Compact, upright, outwardly spreading and mounded plant habit.
2. Freely branching habit.
3. Freely flowering habit.
4. Dark green-colored leaves.
5. Bright cherry rose-colored flowers.
6. Good garden performance.

Plants of the new Zonal *Geranium* differ primarily from plants of the female parent selection in growth habit as plants of the new Zonal *Geranium* are not as compact as plants of the female parent selection.

Plants of the new Zonal *Geranium* differ primarily from plants of the male parent selection in growth habit as plants of the new Zonal *Geranium* are more compact than plants of the male parent selection. In addition, plants of the new Zonal *Geranium* have darker-colored leaves and flowers than plants of the male parent selection.

Plants of the new Zonal *Geranium* can be compared to plants of *Pelargonium×hortorum* 'Clips Rose', disclosed in U.S. Plant Pat. No. 12,411. In side-by-side comparisons conducted in Encinitas, Calif., plants of the new Zonal *Geranium* differed primarily from plants of 'Clips Rose' in the following characteristics:

1. Plants of the new Zonal *Geranium* were more compact than plants of 'Clips Rose'.
2. Plants of the new Zonal *Geranium* and 'Clips Rose' differed in flower color as plants of 'Clips Rose' had rose-colored flowers.

BRIEF DESCRIPTION OF THE PHOTOGRAPHS

The accompanying colored photographs illustrate the overall appearance of the new Zonal *Geranium* plant, showing the colors as true as it is reasonably possible to obtain in colored reproductions of this type. Colors in the photographs may differ slightly from the color values cited in the detailed botanical description which accurately describe the colors of the new Zonal *Geranium* plant.

The photograph at the bottom of the sheet comprises a side perspective view of a typical flowering plant of 'Oglger3147' grown in a container.

The photograph at the top of the sheet is a close-up view of a typical inflorescence of 'Oglger3147'.

DETAILED BOTANICAL DESCRIPTION

The aforementioned photographs and following observations, measurements and values describe plants grown in Encinitas, Calif. in a plastic-covered greenhouse during the spring and under conditions which closely approximate Zonal *Geranium* commercial production. During the production of the plants, day temperatures averaged 24° C., night temperatures averaged 19° C. and light levels averaged 4,000 foot-candles. Plants had been growing for 13 weeks when the photographs and the description were taken. In the detailed description, color references are made to The Royal Horticultural Society Colour Chart, 2001 Edition, except where general terms of ordinary dictionary significance are used.

Botanical classification: *Pelargonium×hortorum* 'Oglger3147'.

Parentage:

*Female, or seed, parent.*—Proprietary selection of *Pelargonium×hortorum* identified as code number 9952, not patented.

*Male or pollen parent.*—Proprietary selection of *Pelargonium×hortorum* identified as code number 9925, not patented.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Medium in thickness, fleshy; white in color.

*Rooting habit.*—Moderate branching; moderately dense.

Plant description:

*General appearance.*—Compact, upright, outwardly spreading and mounding plant habit; densely foliated.

*Growth and branching habit.*—Moderately vigorous to vigorous growth habit. Freely branching habit; about five primary lateral branches develop per plant.

*Plant height, to top of foliar plane.*—About 10.5 cm.

*Plant height, to top of umbels.*—About 16 cm.

*Plant diameter (spread).*—About 20 cm.

*Lateral branches.*—Length: About 5.5 cm. Diameter: About 8 mm. Internode length: About 4 mm. Texture: Pubescent. Strength: Strong. Color: Close to 146B to 146C.

Foliage description:

*Arrangement.*—Alternate; simple.

*Length.*—About 5.5 cm.

*Width.*—About 6.2 cm.

*Shape.*—Reniform.

*Apex.*—Rounde.

*Base*—Cordate.

*Margin.*—Crenate and sinuate.

*Venation pattern.*—Palmate.

*Texture, upper and lower surfaces.*—Densely pubescent.

*Color.*—Developing leaves, upper surface: Close to 146A to 146B. Developing leaves, lower surface: Close to 147B. Fully expanded leaves, upper surface: Close to N137B; venation, close to 146B. Fully expanded leaves, lower surface: Close to 147B; venation, close to 147C. Zonation pattern: Not observed.

*Petiole.*—Length: About 5.1 cm. Diameter: About 2.5 mm. Texture, upper and lower surfaces: Smooth, glabrous. Color, upper and lower surfaces: Close to 147B.

Flower description:

*Flower arrangement.*—Rotate flowers arranged in hemispherical umbels arising from apical leaf axils. Umbels displayed above the foliage on strong peduncles. Flowers face upright to outward; flowers slightly cupped becoming flatter with development.

*Fragrance.*—None detected.

*Quantity of flowers.*—Freely flowering habit; about 16 to 18 flowers per umbel; about five developed umbels per plant at one time.

*Flowering season.*—In Encinitas, Calif., flowering is continuous during the spring and summer.

*Flower longevity.*—Individual flowers last about four to five days on the plant; flowers persistent.

*Umbel height.*—About 4.5 cm.

*Umbel diameter.*—About 8.3 cm.

*Flower diameter.*—About 3.8 cm.

*Flower depth (height).*—About 1.5 cm.

*Flower buds.*—Length: About 1.3 cm. Diameter: About 7 mm. Shape: Ovoid. Color: More pale than 156D.

*Petals.*—Quantity per flower: About eight to ten in one to two whorls. Length: About 2 cm. Width: About 1.8 cm. Shape: Roughly obovate. Apex: Rounded. Base: Attenuate. Margin: Entire. Texture, upper and lower surfaces: Smooth, glabrous; velvety. Color: When opening, upper surface: Close to 71B. When opening, lower surface: Close to 69D. Fully opened, upper surface: Close to 53C; towards the base, close to 51A; venation, close to 53C; color does not fade with development. Fully opened, lower surface: Close to 58C to 58D; at the base, close to 58C; venation, close to 58B to 58C.

*Petaloids.*—Quantity per flower: About ten. Length: About 9 mm to 16 mm. Width: About 2 mm to 8 mm. Shape: Irregular, mostly oblong. Apex: Rounded to acute. Base: Attenuate. Margin: Mostly entire. Texture, upper and lower surfaces: Smooth, glabrous; velvety. Color: When opening, upper surface: Close to 58C. When opening, lower surface: Close to N57C to N57D. Fully opened, upper surface: Close to 53C; at the base, close to NN155D; venation, close to 53C; color does not fade with development. Fully opened, lower surface: Close to 53D; at the base, close to N155D; venation, close to 53D.

*Sepals.*—Quantity per flower: Five, arranged in a single whorl. Length: About 1.1 cm. Width: About 2.5 mm. Shape: Narrowly elliptical. Apex: Acuminate. Base: Attenuate. Margin: Entire. Texture, upper surface:

Smooth, glabrous. Texture, lower surface: Pubescent. Color, upper and lower surfaces: Close to 146B.

*Peduncle* (*umbel stem*).—Length: About 8.2 cm. Diameter: About 3 mm. Strength: Strong. Texture: Pubescent. Color: Close to 187A.

*Pedicel* (*individual flower stem*).—Length: About 2.8 cm. Diameter: About 1 mm. Strength: Strong. Texture: Pubescent. Color: Close to 187B.

*Reproductive organs.*—Androecium: Stamen quantity per flower: About ten. Anther length: About 1 mm. Anther shape: Oblong. Anther color: Close to 183B. Pollen amount: Scarce. Pollen color: Close to 174A. Gynoecium: Pistil quantity per flower: One. Pistil length: About 1.1 cm. Stigma shape: Split into five parts, star-shaped. Stigma color: Close to 187B. Style length: About 2.5 mm. Style color: Close to 187B. Ovary color: Close to 142D.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 2° C. to about 35° C. and have demonstrated good garden performance.

It is claimed:

1. A new and distinct Zonal *Geranium* plant named 'Oglger3147' as illustrated and described.

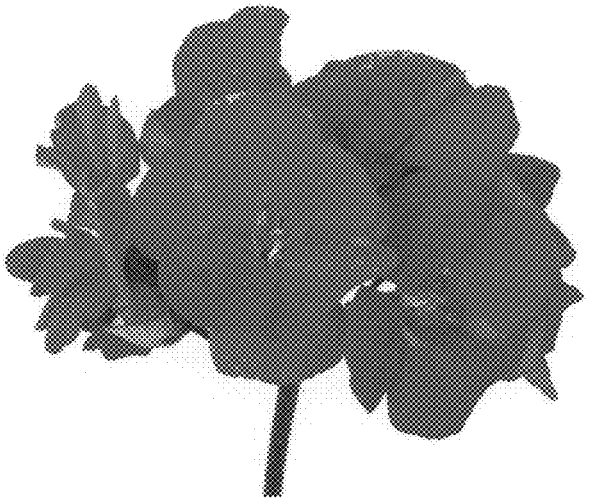
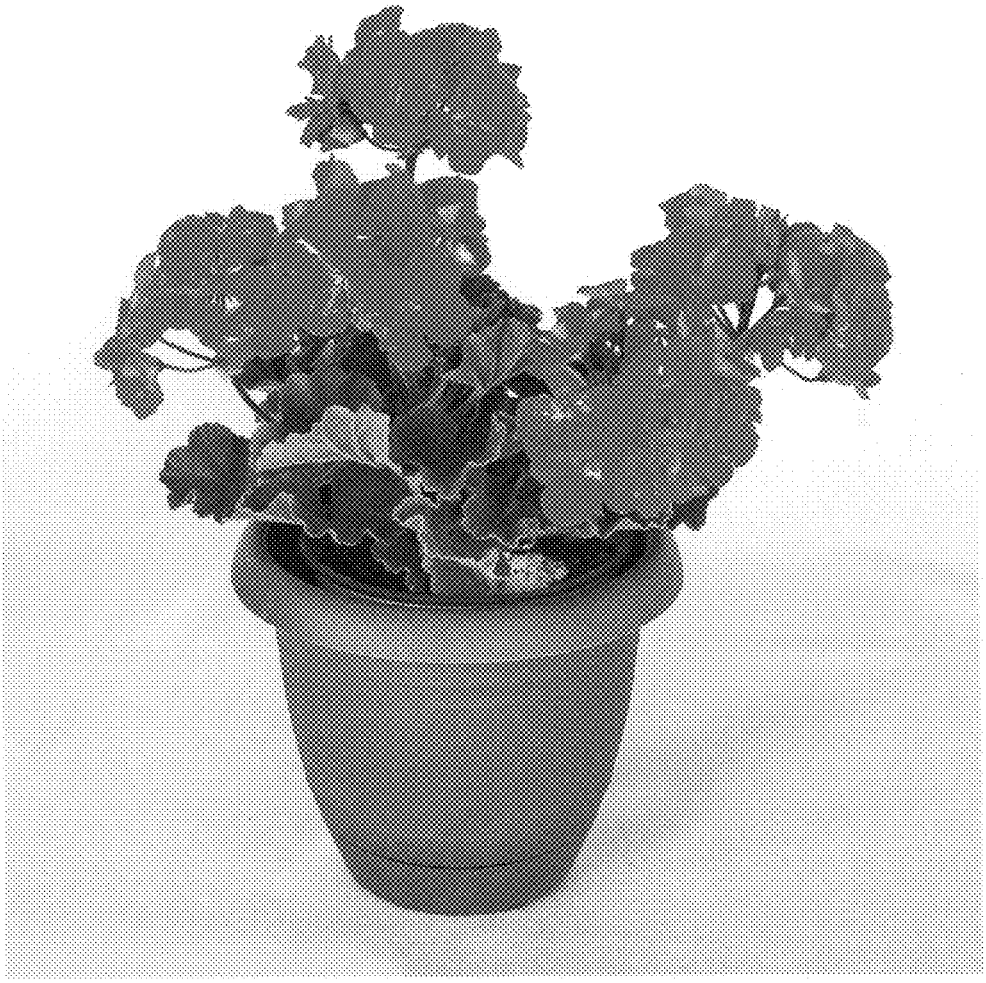

* * * * *